(12) United States Patent
Wang et al.

(10) Patent No.: US 11,590,073 B2
(45) Date of Patent: Feb. 28, 2023

(54) METHODS AND COMPOSITIONS FOR REDUCING THE FEELING OF VAGINAL DRYNESS

(71) Applicant: The Procter & Gamble Company, Cincinnati, OH (US)

(72) Inventors: Samantha Chen-Yee Wang, Cincinnati, OH (US); Larry Richard Robinson, Loveland, OH (US); Kyra L. WilsonHouck, Cincinnati, OH (US); Nery Vanesa Breslin, Hamilton, OH (US); Raphael Warren, Amberly Village, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 16/896,454

(22) Filed: Jun. 9, 2020

(65) Prior Publication Data

US 2021/0378952 A1 Dec. 9, 2021

(51) Int. Cl.
| | |
|---|---|
| *A61K 9/00* | (2006.01) |
| *A61K 9/107* | (2006.01) |
| *A61K 47/12* | (2006.01) |
| *A61K 47/32* | (2006.01) |
| *A61K 47/36* | (2006.01) |
| *A61K 31/695* | (2006.01) |

(52) U.S. Cl.
CPC ............ *A61K 9/0034* (2013.01); *A61K 9/107* (2013.01); *A61K 31/695* (2013.01); *A61K 47/12* (2013.01); *A61K 47/32* (2013.01); *A61K 47/36* (2013.01)

(58) Field of Classification Search
None
See application file for complete search history.

(56) References Cited

U.S. PATENT DOCUMENTS 4,393,871 A * 7/1983 Vorhauer ............. A61K 9/0036
521/905
4,862,726 A * 9/1989 Fooshee .................. B25B 5/163
72/409.01

(Continued)

FOREIGN PATENT DOCUMENTS

| CN | 103405594 A | 11/2013 |
|---|---|---|
| WO | 2008038140 A2 | 4/2008 |

(Continued)

OTHER PUBLICATIONS

Stearyl dimethicone Safety Data Sheet, accessed Oct. 12, 2021 (Year: 2021).*

(Continued)

*Primary Examiner* — Melissa S Mercier
(74) *Attorney, Agent, or Firm* — Melissa G. Krasovec (57) ABSTRACT

A method of reducing the feeling of vaginal dryness is provided. The method includes a female user suffering from vaginal dryness administering a vaginal care composition to her vaginal introitus and, optionally, external vaginal tissues. The vaginal care composition can comprise an oil-in-water emulsion and a silicone wax having a melting temperature of from about 24° C. to about 50° C. The vaginal care composition can also comprise silicone particles. The vaginal care composition can have a viscosity of from about 20,000 cps to about 200,000 cps.

18 Claims, 2 Drawing Sheets

(56) References Cited

U.S. PATENT DOCUMENTS

| | | | |
|---|---|---|---|
| 4,892,726 A * | 1/1990 | Yonekura | A61K 8/025 |
| | | | 424/69 |
| 5,518,733 A | 5/1996 | Lamothe | |
| 5,527,534 A | 6/1996 | Myhling | |
| 7,393,871 B2 * | 7/2008 | Mestroni | C07F 15/0053 |
| | | | 556/137 |
| 11,000,592 B2 * | 5/2021 | Tanner | A61K 31/352 |
| 2004/0078013 A1 * | 4/2004 | Zunker | A61F 2/005 |
| | | | 604/355 |
| 2006/0106044 A1 | 5/2006 | Sommadossi et al. | |
| 2006/0204557 A1 | 9/2006 | Gupta | |
| 2008/0081797 A1 | 4/2008 | Lichtblau | |
| 2009/0088405 A1 | 4/2009 | Kehoe | |
| 2009/0185995 A1 | 7/2009 | Vochecowicz et al. | |
| 2009/0247928 A1 | 10/2009 | Bartning et al. | |
| 2010/0233295 A1 | 9/2010 | Gupta et al. | |
| 2010/0284937 A1 | 11/2010 | Zhao et al. | |
| 2011/0195987 A1 | 8/2011 | Najarian et al. | |
| 2011/0281827 A1 | 11/2011 | Tamarkin | |
| 2012/0100085 A1 | 4/2012 | Klug | |
| 2012/0101135 A1 | 4/2012 | Klug | |
| 2012/0157365 A1 | 6/2012 | Fevola | |
| 2012/0245132 A1 | 9/2012 | Zeng et al. | |
| 2013/0108599 A1 | 5/2013 | Comeaux | |
| 2013/0189196 A1 | 7/2013 | Tamarkin | |
| 2014/0155840 A1 * | 6/2014 | Tseng | A61M 31/00 |
| | | | 604/257 |
| 2014/0178314 A1 | 6/2014 | Tanner | |
| 2015/0190425 A1 | 7/2015 | Goolsbee | |
| 2015/0238415 A1 | 8/2015 | Kiser et al. | |
| 2015/0272986 A1 | 10/2015 | Leif Einar | |
| 2016/0007906 A1 | 1/2016 | Warren | |
| 2016/0017254 A1 | 1/2016 | Cojocariu | |
| 2016/0089314 A1 | 3/2016 | Marsh | |
| 2016/0271109 A1 | 9/2016 | Dreher | |
| 2020/0297622 A1 | 9/2020 | Wang | |
| 2020/0297630 A1 | 9/2020 | Wang | |

FOREIGN PATENT DOCUMENTS

| | | |
|---|---|---|
| WO | 2013017263 A1 | 2/2013 |
| WO | 2016156403 A1 | 10/2016 |
| WO | 2017098396 A1 | 6/2017 |

OTHER PUBLICATIONS

Lee (5 Things that Can Cause Vaginal Dryness, Everyday Health, Apr. 12, 2016). (Year: 2016).*

All Office Actions; U.S. Appl. No. 16/896,474.

All Office Actions; U.S. Appl. No. 16/896,440.

Edwards D, Panay N. "Treating vulvovaginal atrophy/genitourinary syndrome of menopause: howimportant is vaginal lubricant and moisturizer composition?"; Climacteric. Apr. 2016;19(2):151-61. doi: 10.3109/13697137.2015.1124259. Epub Dec. 26, 2015.

International Search Report and Written Opinion; Application Serial No. PCT/US2019/015050, dated Jul. 2, 2019; 16 Pages.

U.S. Appl. No. 16/896,440, filed Jun. 9, 2020, Wang, et al.

U.S. Appl. No. 16/896,474, filed Jun. 9, 2020 Wang, et al.

* cited by examiner

METHODS AND COMPOSITIONS FOR REDUCING THE FEELING OF VAGINAL DRYNESS

TECHNICAL FIELD

Described herein are methods and compositions for reducing the feeling of vaginal dryness and more particularly, a vaginal care composition comprising a silicone wax and/or silicone particles.

BACKGROUND

Estimates indicate that by 2030 there will be about 1.2 billion menopausal and post-menopausal women in the world. Given that the average age at which menopause occurs has remained the same and that life expectancy among women has generally increased, the number of post-menopausal women is expected to grow. As such, there is increasing concern surrounding the conditions and symptoms experienced by perimenopausal, menopausal, post-menopausal women, and the need for treatment therefore is growing as well.

Menopause is generally defined as 12 months after a woman's last menstrual period. The process leading to menopause (commonly known as peri-menopause) can be a gradual process, however. As is well known, peri-menopause and menopause can be accompanied by hot flashes, night sweats, mood changes, stress, fatigue, irritability, and difficulty with memory. Furthermore, menopause is associated with a decrease in estrogen production. Decreased estrogen blood levels can result in changes to both the internal and external genitalia (i.e., vulvar-vaginal region), including vaginal atrophy and a thinning of the vaginal and urethral mucous membrane, a loss in vaginal elasticity, and a reduction in gland secretion, which may be accompanied by a decrease in tissue hydration. Some estimate that up to 57% of perimenopausal and post-menopausal woman suffer from vaginal atrophy. Vaginal atrophy can facilitate urogenital infections and may also result in vaginal irritation, burning, dryness, itching, odor, and pain during sexual intercourse (dyspareunia), thus greatly impacting a woman's quality of life.

There are a variety of solutions that have been proposed to address the above-described vaginal conditions and symptoms. Prescription-based remedies have included hormone replacement therapy, which can include an estrogen supplement with or without progesterone that is administered deep within the vaginal canal. While hormone therapies have shown positive effects in the treatment of vaginal atrophy, some women continue to experience menopausal symptoms, and for many women, such treatment can prove to be too expensive. Hormone replacement therapy is generally limited by consumer fear and by contraindications such as a history of cancer and thromboembolism. Moreover, due to the nature of the condition, women may feel uncomfortable and/or embarrassed discussing the above-described symptoms and may avoid seeking a doctor's consultation. Additionally, many women stop annual visits to gynecologists, leaving their primary care family physician as the main resource for potential treatment, yet primary care physicians typically fail to address or treat menopausal symptoms since menopause is viewed as a "natural" part of aging.

Current over-the-counter approaches to relieving vaginal dryness include the application of sexual lubricants for reducing discomfort during intimacy (e.g., Replens® Silky Smooth Personal Lubricant, Astroglide®, K-Y® gels and lubricants) or vaginal moisturizers (e.g., Replens® Long Lasting Moisturizer and Replens® Moisture Restore External Comfort Gel, or HyaloGyn/HyaloFemme, available from Fidia Farmaceutici SpA and both supplied with disposable applicators to place in the vaginal canal).

While the aforementioned over-the-counter solutions may be useful, some forms may not prioritize women's intimate health or the usage experience. For example, current products are designed to act rapidly to provide short-term relief on an as-needed basis (e.g. prior to sex) and may not provide the long-lasting moisturizing and lubricity desired. It is known that moisturizers generally rehydrate dry vaginal epithelial tissue and are absorbed into the epithlia, but do not provide a desired lubricity. In addition, current vaginal moisturizer products include mucoadhesive polymers that bind to, and hold water at, the vaginal epithelial surface in order to hydrate the underlying cells and are formulated to be applied deep within the vaginal canal every 3 days. However, plunger-type devices for delivering the product deep within the vaginal canal may be an added mechanical irritant and may compromise the fragile tissue. Moreover, mucoadhesive polymers have been reported by female users to feel sticky when used in a vaginal product. Sexual lubricants act to provide short-term relief from vaginal dryness and related pain during sex. For instance, water and silicone based lubricants are designed to be applied shortly before sexual activity, which can impact the overall experience and hinder spontaneity, and may not provide long-lasting benefits because they are typically wiped or washed off after use. In addition, typical sexual lubricants have a low viscosity, making them difficult to apply to the desired location and tend to leak from the site of application. Silicone-based lubricants are also known to stain fabrics, which can be undesirable to consumers, and may not be compatible with silicone vaginal applicators or devices. Finally, the methods of application (e.g., digitally) and marketing aesthetics (e.g., as adjuncts to sex) of current vaginal moisturizers and sexual lubricants can also serve as barriers to women seeking treatment.

While it is known that vaginal atrophy and dryness can cause pain and discomfort during sex, it is less widely discussed that vaginal atrophy can also cause discomfort and pain during everyday activities such as walking, exercising, or sitting/standing. Women suffering from vaginal atrophy have reported experiencing vaginal dryness that can cause the vaginal tissue to stick together and/or to clothing, which can be uncomfortable and/or painful and can hinder daily activities. Women experiencing vaginal atrophy are also limited in what kinds of clothing they can wear; even jeans or tighter pants can cause pain and discomfort. Additionally, many women going through peri-menopause and in menopause are not in partnered relationships and do not engage in sexual activity due to pain, lack of partner, self-esteem, or low libido caused by decreased estrogen, which renders a sexual lubricant unnecessary.

As such, there remains a need for improved methods and compositions for reducing the feeling of vaginal dryness that can provide moisturization and lubricity throughout the entire day without staining clothing or leaking from the site of application. In particular, there is a need for a method of reducing the feeling of vaginal dryness that involves applying a vaginal care composition that can provide a long-lasting moisturizing and lubricity benefit, preferably for from about 3 hours to about 48 hours, and can help to alleviate pain/discomfort during daily activities, without the need for acute use of sexual lubricants.

SUMMARY

A method of reducing the feeling of vaginal dryness comprises administering a vaginal care composition to a female user in need thereof; wherein the vaginal care composition comprises: (a) an oil-in-water emulsion; (b) a silicone wax having a melting temperature of from about 24° C. to about 50° C.; and (c) a thickener comprising a polyacrylamide polymer.

A method of reducing the feeling of vaginal dryness comprises (a) a female user providing an amount of a virginal care composition on at least a portion of the outer surface of an applicator; and (b) administering at least a portion of the amount of the vaginal care composition to her vaginal introitus and, optionally, one or more of her vulva, vestibule, labia majora, labia minora, or external urogenital tract while grasping and manipulating the applicator; wherein the vaginal care composition comprises an oil-in-water emulsion and a silicone wax having a melting temperature of from about 24° C. to about 50° C.

A method of restoring vaginal moisture and lubrication comprises administering a vaginal care composition to a female user in need thereof; wherein the vaginal care composition comprises: (a) an oil-in-water emulsion; (b) silicone particles having an average particle size of from about 1 μm to about 15 μm; and (c) a thickener comprising a polyacrylamide polymer.

A kit for reducing the feeling of vaginal dryness comprising: a vaginal care composition and an applicator for applying the vaginal care composition to a vaginal introitus and, optionally, external vaginal tissues; wherein the vaginal care composition comprises: (a) an oil-in-water emulsion; (b) a silicone wax having a melting temperature of from about 24° C. to about 50° C.; and (c) a thickener comprising a polyacrylamide polymer.

A method of reducing the feeling of vaginal dryness comprises (a) a female user providing an amount of a vaginal care composition on at least a portion of an applicator; and (b) administering at least a portion of the amount of the vaginal care composition to her vaginal area while grasping and manipulating the applicator; wherein the vaginal care composition comprises an oil-in-water emulsion and a silicone wax having a melting temperature of from about 24° C. to about 50° C.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION

Consumers are looking for improved ways to reduce vaginal dryness that can provide long-lasting moisturizing and lubricity benefits using a once-a-day application regimen with a product having a non-sticky texture, without the need for conventional sexual lubricants that are used each time symptoms or discomfort is felt. It has been found that a vaginal care composition comprising an oil-in-water emulsion and silicone can be applied daily to the vaginal introitus and, optionally, the external vaginal tissue to provide a feeling of moisturization and lubricity throughout the day, even after wiping and/or urination, thus making every day activities more comfortable. In particular, it was surprisingly found that a vaginal care composition comprising an oil-in-water emulsion and a silicone wax and/or silicone particles can be used to reduce the feeling of vaginal dryness.

Silicone waxes are known to leave a heavy residue when applied to the skin, which consumers often find undesirable in conventional skin care or facial products. However, it was found that a vaginal care composition comprising a silicone wax that melts at or near body temperature can provide acute lubricity and also the chronic benefit of healing/improving the vaginal epithelium without the negative drawbacks of current vaginal moisturizers or sexual lubricants. Without being limited by theory, it is believed that the silicone wax can help to coat the vaginal tissue, can reduce friction during movement, and/or can help seal and protect the skin barrier without being sticky. Silicone waxes can be solid at room temperature, helping to provide sufficient viscosity to the vaginal care composition to allow application to the body, yet can melt at body temperature after application, providing a long-lasting, soothing feel during daily activities. It is believed that the hydrocarbon pendant groups can help the silicone wax persist on the skin longer than traditional silicones, providing a coated and lubricated feel throughout the day. The vaginal care composition can also optionally comprise silicone particles. It is thought that during application of the vaginal care composition, the silicone particles can roll over the tissue like ball bearings, thus reducing friction and irritation during application.

Described herein is a vaginal care composition comprising an oil-in-water emulsion, a silicone wax and/or silicone particles that can be applied to the vaginal introitus and, optionally, external vaginal tissues such the vulva, vestibule, labia majora, labia minora, or external urogenital tract to reduce the feeling of vaginal dryness. In one aspect, the vaginal care composition can provide relief of vaginal dryness for about 4 hours to about 36 hours, alternatively for about 6 hours to about 24 hours, alternatively for about 12 hours to about 24 hours. Also described herein is a kit comprising a vaginal care composition and a delivery device, such as an applicator, for applying the vaginal care composition.

All percentages are by weight of the vaginal care composition, unless specifically stated otherwise. All ratios are weight ratios, unless specifically stated otherwise. All ranges are inclusive of narrower ranges and combinable. Delineated upper and lower range limits are interchangeable to create further ranges not explicitly delineated. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions of the disclosure can comprise, consist essentially of, or consist of, the components as well as optional ingredients described herein. As used herein, "consisting essentially of" means that the applicator, composition, or component may include additional ingredients or features, but only if the additional ingredients or features do not materially alter the basic and novel characteristics of the claimed applicators, compositions, or methods. As used in the description and the claims, the singular forms "a," "an," and "the" are intended to include the plural forms as well, unless the context clearly indicates otherwise. Unless otherwise defined, all technical and scientific terms used herein have the same meaning as commonly understood by one of ordinary skill in the art to which this invention belongs.

As used herein, "aromatic alcohol preservative" includes molecules that contain at least one benzyl moiety, a single hydroxyl moiety, and is free of carboxylates. The hydroxyl moiety may be directly bonded to the benzyl moiety or on a side chain.

As used herein, "estrogen agent" means any natural or synthetic estrogen hormone (e.g., estrone, estradiol and estriol), metabolites thereof, esters thereof, analogues thereof, phytoestrogens (e.g., isoflavones, coumestans, prenylflavonoids), estrogen precursors (e.g., dehydroepiandrosterone) and/or any compound which binds to an estrogen receptor or which otherwise exhibits at least mild or weak estrogen-like effects, including selective estrogen receptor modulators ("SERM") such as, for example: afimoxifene (4-hydroxytamoxifen), arzoxifene, bazedoxifene, clomifene, femarelle (DT56a), lasofoxifene, ormeloxifene, raloxifene, tamoxifen, toremifene, mifepristone (RU486), VA2914, ulipristal, Proellex, Asoprisnil, and CDB-4124.

As used herein, "grippable portion" means a portion having an outer shape and size which may be grasped by 2 or more fingertips of a human hand to manipulate the applicator in use.

As used herein, "introitus" means the vaginal opening in a human that extends from the entrance of the vaginal canal to 35 millimeters (mm) into the vaginal canal.

As used herein, "preservative enhancing agent" means any molecule that is not registered for use in cosmetic compositions with the appropriate regulatory body as a preservative but demonstrates improved anti-bacterial, anti-microbial, or anti-fungal benefits when included in an oil-in-water vaginal care composition.

As used herein, "mucoadhesive" refers to the phenomenon where a natural or synthetic substance applied to a mucosal epithelium, adheres, usually creating a new interface, to the mucus layer. Generally, mucoadhesion can be achieved via physical or chemical processes or both.

As used herein, "perimenopausal" woman is one who in the absence of hormone replacement therapy or other medication would experience a change in her intermenstrual cycle interval and have associated symptoms of estrogen deficiency, such as vasomotor flushes, vaginal dryness and/or worsening premenstrual syndrome. Also included are women who in the absence of hormone replacement therapy or other medication would experience less than 12 months amenorrhea.

As used herein, "pharmacologically effective amount", "therapeutically effective amount" or simply "effective amount" means the amount of a composition, or ingredient thereof, effective to produce the intended pharmacological, therapeutic or preventive result.

As used herein, "postmenopausal" woman is one who in the absence of hormone replacement therapy or other medication would experience at least 12 months of amenorrhea.

As used herein, "progesterone agent" means any natural or synthetic progesterone hormone, metabolites thereof, analogues thereof, progesterone precursors and/or any compound which binds to a progesterone receptor or which otherwise exhibits at least mild or weak progesterone-like effects, including selective progesterone receptor modulators ("SPRM") such as, for example, telapristone.

As used herein, "rotational symmetry" means the applicator, or a portion thereof such as the insertion portion or the grippable portion, has an overall shape that looks the same thru some rotation (e.g., 45°, 90°, 135°, 180°, 225°, 270°, 315°, or 360°) about its longitudinal axis. For example, an applicator that has an overall shape that looks the same thru a rotation of 45° is considered rotationally symmetrical thru that 45° rotation. Likewise, an applicator that has an overall shape that looks the same thru one full rotation is considered rotationally symmetrical thru 360°. The reference to rotational symmetry herein, unless stated otherwise, ignores surface features such as print, coloring, coatings, text, graphics, dosing indicators, insertion indicators, surface textures, and surface finishes.

As used herein, "substantially free" means a component or material is present in amount less than about 0.1%, 0.05%, 0.025%, 0.01%, or 0.001% by weight of the vaginal care composition.

As used herein, "taper" means to become smaller toward one end. An applicator, or feature thereof such as the insertion portion, may have a taper that is gradual, substantial, intermittent, continuous and combinations thereof. For example, an applicator is considered to taper from the maximum width to the tip merely if the bulk cross-sectional area (e.g., inclusive of both solid cross-sectional area and void cross-sectional area) at the tip is less than the bulk cross-sectional area at the maximum width, even though, for example, the bulk cross-sectional area may intermittently increase or remain constant between the maximum width and the tip.

As used herein, "treating" means relieving or alleviating.

As used herein, "vaginal area" means the vaginal canal and the vulva (or pudendum), a collective term for the external female genital organs that are visible in the perineal area including the vaginal orifice, vaginal introitus, vulvar vestibule, labia majora, labia minora, external urogenital tract, urethral orifice, clitoris, and vulvar skin which is bounded longitudinally by the mons pubis and anus and bounded laterally by the genitocrucal folds.

As used herein, "vaginal canal" refers to the tissue proximal to the vaginal introitus.

As used herein, "vaginal care composition" means any composition that is suitable for application to the vaginal introitus and/or one or more of the vulva, vestibule, labia majora, labia minora, and/or external urogenital tract and which is useful for treating or reducing vaginal dryness.

Vaginal Care Compositions

The vaginal care compositions described herein are suitable for application to the vaginal introitus and, optionally, the external vaginal tissues. The vaginal care composition is preferably non-irritating and substantially free of ingredients that are less suitable for application to these tissues.

The vaginal care composition may comprise a preservative system comprising one or more preservatives and a preservative enhancing agent. A preservative can be understood to be a chemical or natural compound (or combination of compounds) that can help inhibit the growth of microbes, thus protecting the consumer during intended product use and/or increasing the shelf-life of the composition. In one aspect, the preservative(s) can be non-irritating when applied to the vaginal introitus/vulvar vestibule. The preservative(s) can be selected from the group consisting of aromatic alcohol preservatives, organic acid preservatives, salts thereof, and combinations thereof.

Organic acid preservatives are organic molecules with at least one carboxyl group. In one aspect, the organic acid preservatives can be soluble in water and can have a water solubility at ambient conditions of at least 0.1, alternatively at least 0.5, alternatively at least 1 g/100 ml water. Non-limiting examples of organic acid preservatives can include glutamic acid, malonic acid, phthalic acid, fumaric acid, formic acid, malic acid, heptanoic acid, ascorbic acid, oxalic acid, succinic acid, glutaric acid, adipic acid, propionic acid, butyric acid, pentanoic acid, hexanoic acid, pimelic acid, suberic acid, acetic acid, carbonic acid, lactic acid, salicylic acid, benzoic acid, sorbic acid, citric acid, 4-hydroxybenzoic acid, dehydroacetic acid, undecylenic acid, salts thereof, and mixtures thereof. Salts of the organic acid preservative may include any cationic counterion. Non-limiting examples of organic acid preservative salt counter ions can include sodium, ammonium, calcium, magnesium, potassium, and silver. In one aspect, the organic acid preservative can be selected from the group consisting of salicylic acid, benzoic acid, sorbic acid, citric acid, propionic acid, 4-hydroxybenzoic acid, dehydroacetic acid, formic acid, undecylenic acid, salts thereof, and mixtures thereof. In one aspect, the organic acid preservative can be selected from the group consisting of benzoic acid, sodium benzoate, citric acid, sodium citrate, sodium salicylate, salicylic acid, sorbic acid, and mixtures thereof. In one aspect, a combination of an acid and a salt of the same organic acid preservative, such as citric acid and sodium citrate, can be used. In one aspect, a combination of two or more organic acid preservatives, such as citric acid, sodium citrate, and sodium benzoate, can be used. Without being limited by theory, it is believed that the combination of the acid and salt form of the same organic acid preservative can allow for the vaginal care composition to be acidic while providing a buffered system.

The preservative can be an aromatic alcohol preservative. Non-limiting examples of aromatic alcohol preservatives can include biphenyl-2-ol, butyl 4-hydroxybenzoate, propyl 4-hydroxybenzoate, ethyl 4-hydroxybenzoate, methyl 4-hydroxybenzoate, triclosan, chloroxylenol, o-cymen-5-ol, chlorophene, dichlorobenzyl alcohol, phenoxyethanol, benzyl alcohol, phenoxyisopropanol, benzylhemiformal, and combinations thereof. In one aspect, the aromatic alcohol preservative can be selected from the group consisting of benzyl alcohol, phenoxyethanol, propyl 4-hydroxybenzoate, ethyl 4-hydroxybenzoate, and combinations thereof.

The vaginal care composition can comprise less than about 3% of a preservative, alternatively less than about 2%, alternatively less than about 1.8%, alternatively less than about 1.6%, all by weight of the vaginal care composition. The vaginal care composition can comprise from about 0.1% to about 3% of a preservative, alternatively from about 0.5% to about 2%, alternatively from about 1.2% to about 1.6%, all by weight of the vaginal care composition.

The vaginal care composition can comprise less than about 3% of a preservative system, alternatively less than about 2%, alternatively less than about 1.8%, alternatively less than about 1.6%, all by weight of the vaginal care composition. The vaginal care composition can comprise from about 0.1% to about 3% of a preservative system, alternatively from about 0.5% to about 2%, alternatively from about 1.2% to about 1.6%, all by weight of the vaginal care composition.

In one aspect, the vaginal care composition can comprise a preservative enhancing agent. The preservative enhancing agent can comprise sorbitan caprylate. In one aspect, the preservative enhancing agent can consist essentially of sorbitan caprylate. An exemplary sorbitan caprylate is manufactured by Clariant (Muttenz, Switzerland) under the designation VELSAN® SC. The vaginal care composition can comprise from about 0.01% to about 3% preservative enhancing agent, alternatively from about 0.01% to about 1%, alternatively from about 0.05% to about 0.8%, alternatively from about 0.1% to about 0.3%, all by weight of the vaginal care composition.

In one aspect, the preservative enhancing agent can be substantially free of diols. Without being limited by theory, it is believed that diols at some levels can be irritating to the vaginal introitus.

The preservative system may also include additional compounds, for example chelating agents, such as ethylenediamine tetraacetic acid (EDTA) and its salts, or diethylene triamine pentaacetic acid (DTPA) and its salts.

In one aspect, the vaginal care composition can have a pH of from about 4.0 to about 5.5, preferably from about 4.3 to about 5.0, more preferably 4.4 to about 4.8. One advantage to using a pH in this range is that the pH of the vaginal care composition will be close to the pH of the vaginal introitus. It is believed that if the pH is lower than this range the composition may be irritation to the vaginal introitus/external vaginal tissues. It is believed that if the pH is above this range, the preservative system may not be as effective and higher levels of the preservative system and/or additional preservatives may be needed to prevent microbial growth.

The vaginal care composition may be provided, for example, in the form of a spreadable gel, serum, lotion, paste, or cream. In one aspect, the vaginal care composition can be in the form of an oil-in-water emulsion. An oil-in-water emulsion may provide a sensorial feel that is light and non-greasy, but still delivers moisturization and lubricity without aesthetic negatives like stickiness or heavy residue commonly associated with oil-based compositions and/or mucoadhesive ingredients. Further, the vaginal care compositions may further comprise one or more vaginal care agents. The vaginal care composition may comprise one or more water soluble ingredients.

The vaginal care composition can comprise water, one or more oils, and, optionally, one or more vitamins and/or pro-vitamins (e.g., a substance that may be converted to a vitamin by metabolic processes), one or more thickeners, one or more emulsifiers, one or more humectants, one or more lubricants (which may also be in the form of an oil), one or more moisturizers (which may also be in the form of an oil), one or more feel modifiers (e.g., particulates, powders and film forming agents). The vaginal care composition preferably provides a suitable viscosity, dry feel, moisturization/emolliency benefits, suitable lubricity, and/or vaginal health benefits.

The vaginal care composition may comprise water in an amount greater than about 50%, or greater than about 60%, or from about 50% to about 95%, or from about 60% to about 90%, or from about 65% to about 80%, all by weight of the vaginal care composition. The water may provide a carrier for water soluble ingredients as well as a moisturization benefit.

The vaginal care composition may comprise one or more emollients. An emollient can help skin maintain a soft, smooth appearance. Emollients can be deposited onto the skin and remain at its surface as a thin protective layer, providing moisturizing and/or lubricating benefits. Non-limiting examples of emollients can include botanical oils, hydrocarbon oils, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The vaginal care composition may comprise less than about 30%, or from about 1% to about 20%, or from about 5% to about 15%, or from about 10% to about 15% emollient, all by weight of the vaginal care composition. The vaginal care composition can comprise from about 0.05% to about 5% emollient, or from about 0.1% to about 2%, or from about 0.2% to about 1%, by weight of the vaginal care composition.

In one aspect, the botanical oil can be derived from one or more plant source materials, such as the leaf, root, bark, stem, flower, or seed of a plant. The botanical oil may be a seed oil, a nut oil, a flower oil, or a leaf oil. The botanical oil may comprise polyunsaturated fatty acids, preferably omega-3 (e.g., α-linolenic acid) and/or omega-6 fatty acids. The botanical oil may be a coconut oil, an evening primrose oil, a sunflower seed oil, a safflower oil, and combinations thereof, which contain omega-3 and/or omega-6 fatty acids. Other non-limiting examples of suitable botanical oil materials can include oleic canola Oil (*Brassica campestris, B. napus, B. rapa*; characterized by having an oleic content greater than 70%, e.g., hi oleic canola oil, very high oleic canola oil, or partially hydrogenated canola oil), manila kernel oil (*Sclerocarya birrea*), palm oil (*Elaeis Guineensis* Oil), palm olein, palm stearin, palm superolein, pecan oil, pumpkin seed oil, sesame oil (*Sesamum indicum, S. oreintale*), soybean oil (*Glycine max*, e.g., hi oleic soybean, low linolenic soybean oil, partially hydrogenated), and mixtures thereof. The vaginal care composition may comprise from about 0.05% to about 5% of botanical oil(s), or from about 0.1% to about 2%, or from about 0.2% to about 1%, by weight of the vaginal care composition.

The vaginal care composition may further comprise one or more silicone oils. Silicone oils are liquids comprising one or more polymerized siloxanes or silicone polymers (e.g., polysiloxanes, polydimethylsiloxanes (PDMS) and combinations thereof). The silicone oil may comprise dimethicone, dimethiconol (a high molecular weight silicone gum), and combinations thereof, one example being Dow Corning® 1503 Fluid (available from Dow Corning Corp.) which comprises a combination of dimethicone and dimethiconol. The vaginal care composition may comprise from about 0.1% to about 4% silicone oil(s), alternatively from about 0.5% to about 3%, alternatively from about 1% to about 3%, all by weight of the vaginal care composition. One advantage to including a silicone oil is that it can provide a lubrication benefit. This can be important because a silicone oil can impart an acute benefit during sexual intercourse, which could be painful without a lubricating component. A silicone oil can also impart an acute benefit during and after application; the lubrication benefit allows the product to glide and spread easily during application and lubricates the vaginal tissue during daily activities.

The vaginal care composition may comprise one or more vitamins and/or pro-vitamins for providing a vaginal health benefit. Some non-limiting examples include niacinamide, panthenol, vitamin B3, vitamin B5, vitamin E and derivatives thereof. The vaginal care composition may comprise from about 0.1% to about 7%, or from about 0.5% to about 6%, or from about 2% to about 5% by weight of the vaginal care composition of vitamin(s) and/or pro-vitamin(s).

The vaginal care composition may comprise one or more humectants, such as glycerol. The humectant may be provided in an amount from about 0.1% to about 20%, or from about 1% to about 15%, or from about 8% to about 12%, all by weight of the vaginal care composition. Alternatively, the humectant can be provided in an amount from about 0.1% to about 5%, alternatively from about 0.5% to about 1%, all by weight of the vaginal care composition. Other humectants which may be provided include other polyhydroxy alcohols, polyethylene glycols, aloe vera in any of its forms, hyaluronic acid or salts thereof, and combinations thereof. The humectants may provide a moisturizing benefit. Without being limited by theory it is believed that this moisturizing benefit can be important in the vaginal context since moisture in vaginal tissue must be retained throughout the day, even after urination and wiping. In one aspect, the vaginal care composition can comprise from about 0.1% to about 2% hyaluronic acid or a salt thereof, alternatively from about 0.3% to about 1%, all by weight of the vaginal care composition. It was previously believed that hyaluronic acid, or a salt thereof, at levels higher than about 0.1% in a skin care composition can leave an undesirable sticky residue on the skin. However, it was surprisingly found that hyaluronic acid could be used in a vaginal care composition at a level of greater than about 0.1% without feeling sticky.

The vaginal care composition may further comprise one or more silicone particles to impart desirable feel characteristics to the vaginal care composition. In some embodiments, the vaginal care composition can comprise siloxane particles (e.g., polymethylsilsesquioxane) having an average particle size from about 1 μm to about 15 μm, alternatively from about 2 μm to about 10 μm, alternatively from about 4 μm to about 8 μm. The particles may be in the form of mono-disperse microspheres. The polymethylsilsesquioxane particles are sometimes also referred to as silicone resins. Some non-limiting examples of polymethylsilsesquioxane particles can include TOSPEARL® series from Momentive Performance Materials, Inc. (Waterford, N.Y.), including TOSPEARL® 2000, TOSPEARL® 145, TOSPEARL® 150, TOSPEARL® 1320, and the like. One advantage to including silicone particles is that the particle size and nature of the particles can impart a dry feel upon application. Without being limited by theory, it is believed that the silicone particles may also facilitate the ease of spreading, rubbing or otherwise applying the vaginal care composition to the vaginal tissues of interest. The vaginal care composition can comprise from about 0.01% to about 3% silicone particles, alternatively from about 0.1% to about 1.25%, alternatively from about 0.2% to about 0.75%, all by weight of the vaginal care composition.

The vaginal care composition may further comprise a silicone wax. Silicone waxes are materials that contain at least one silicon atom which are solid or semisolid at room temperature. In one aspect, the silicone wax can have a melting temperature ranging from about 24° C. to about 105° C., alternatively from about 25° C. to about 40° C., alternatively from about 28° C. to 35° C. The melting temperature of the silicone wax can be measured according to the drop melting point method of ASTM D127 (Jan. 1, 2015).

In one aspect, the silicone was can be an organopolysiloxane having the following formula (I):

in which:

$R_9$, $R_{11}$, and $R_{12}$ are, independently of one another, chosen from a $(C_1-C_{30})$ alkyl moiety, a $(C_1-C_{30})$ alkoxy moiety, and a $(C_6-C_{30})$ aryl moiety, $R_{10}$ is chosen from a $(C_2-C_{36})$ alkyl moiety, a $(C_2-C_{36})$ alkoxy moiety, a $(C_2-C_{36})$ alkyl moiety, and a $(C_2-C_{36})$ alkoxy moiety which is substituted by an ester group, it also being possible for $R_{10}$ to be a methyl moiety when Z is a $(C_2-C_{30})$ alkyl moiety, a $(C_2-C_{30})$ alkoxy moiety, and a $(C_2-C_{30})$ ester, Z is chosen from a $(C_1-C_{30})$ alkyl moiety, a $(C_1-C_{30})$ alkoxy moiety, a $(C_6-C_{30})$ aryl moiety, and a $(C_1-C_{30})$ ester, u is 0 or an integer between 1 and 100, and v is an integer between 3 and 100.

Non-limiting examples of suitable silicone waxes can include ABIL® Wax series of alkyl silicones from Evonik Industries AG (Essen, Germany), including ABIL® Wax 2434 (stearoxy dimethicone), ABIL® Wax 2440 (behenoxy dimethicone), and ABIL® Wax 9810P ($C_{24-28}$ alkyl dimethicone). Additional examples of suitable silicone waxes include Dow Corning® 2503 Wax (stearyl dimethicone and octadecene), Dow Corning® SW-8005 C30 Resin Wax ($C_{30-45}$ alkyldimethylsilyl polypropylsilsesquioxane), and Dow Corning® 580 Wax (Stearoxy trimethylsilane and stearyl alcohol) all from Dow Corning Corp. (Carrollton, Ky.), VP 1622 (stearoxy dimethicone) from Wacker Chemie AG (Munich, Germany). Preferred silicone waxes include semisolid waxes such as Silwax® L118 (stearyl dimethicone) available from Siltech (Toronto, Ontario, Canada) with a melting temperature of about 30° C.

In one aspect, the silicone wax may be selected to impart a dry feel when touched initially and a lubricious feel in use (i.e., upon melting). It can be preferred to use silicone waxes that are solid or semisolid at room temperature but melt upon application to the body, especially the vaginal area which may be at a warmer temperature when occluded (for example under clothing) than typically exposed skin like the hands and face. The silicone wax, upon melting, may also facilitate the ease of spreading, rubbing or otherwise applying the vaginal care composition to vaginal tissue. One advantage to using such silicone waxes is that they can provide unique and preferred feel benefit due to the softening or melting during the application process. Without wishing to be bound by theory, it is believed that during the application process, the silicone wax can melt when applied to skin, forming a layer of silicone that provides a smooth, slick feel.

The vaginal care composition can comprise from about 0% to about 20% silicone wax, alternatively from about 0.1% to about 10%, alternatively from about 0.5% to about 5%, all by weight of the vaginal care composition.

The vaginal care composition may further comprise one or more emulsifiers. Some non-limiting examples of emulsifiers can include cationic surfactants, anionic surfactants, non-ionic surfactants, polyethylene glycol, polyethylene glycol, polypropylene copolymers, alkyl glucosides, ethoxylated fatty acids and, combinations thereof. The vaginal care composition can comprise from about 0.005% to about 5% emulsifier, alternatively from about 0.01% to about 3%, alternatively from about 0.1% to about 1%, all by weight of the vaginal care composition. In one aspect, the emulsifier can be polyethylene glycol (PEG) 100 stearate, cetearyl glucoside, and combinations thereof.

The vaginal care composition can comprise one or more thickeners. The thickeners can be provided in amounts to facilitate achieving the desired viscosity in combination with the other ingredients. The thickeners may be provided in an amount from about 0.5% to about 10%, alternatively from about 1% to about 8%, alternatively from about 1.5% to about 5%, all by weight of the vaginal care composition. One advantage to including a thickener at this level is that it can help provide sufficient viscosity, allowing the vaginal care composition to be applied to a portion of the outer surface of a delivery device, such as an applicator, and administered to the vaginal introitus, and optionally external vaginal tissues. If the viscosity is too low, the vaginal care composition may be difficult to apply to the delivery device and/or administer to the body, causing a mess on hands and countertops which may be unacceptable to consumers. Without being limited by theory, it is also believed that at this level of thickener, the vaginal care composition will remain on the vaginal tissue, thus providing longer lasting moisturizing benefits. At lower levels of thickener, it is thought that the vaginal care composition may dry too quickly after application, thus hindering the ability for the vaginal care composition to provide the desired vaginal health benefits. At higher levels of thickener, the vaginal composition may be difficult to expel from packaging, be difficult to spread with minimal force, or may be difficult to wash or remove from the surface of the delivery device and/or hands.

In some instances, it may be desirable to exclude from the vaginal care compositions herein thickeners and/or other materials that have hydroxyl or carboxyl functional moieties, which may impart undesirable feel properties (e.g., stickiness, heavy residue feel, non-lubricious feel) when applied to the labia and/or introitus. Accordingly, it may be desirable to formulate the vaginal care compositions herein to be substantially free of such materials. Some non-limiting examples of mucoadhesive materials that may be undesirable for use herein include polyacrylates (e.g., Makimousse-21 and -25 brand sodium polyacrylate starch from Kobo), carbomers (e.g., Carbopol® from Lubrizol), polycarbophils (e.g., Noveon® from Lubrizol), poly(methylvinyl ether/maleic anhydride) copolymers, acidic synthetically modified natural polymers (e.g., carboxymethylcellulose), basic amine-bearing polymers (e.g., chitosan); acidic polymers obtainable from natural sources (e.g., alginic acid, pectin, tragacanth gum, and karaya gum); and neutral synthetic polymers (e.g., polyvinyl alcohol and polyvinylpyrrolidone).

In one aspect, the thickener can be non-mucoadhesive. In one aspect, the thickener can be selected from the group consisting of a polyacrylamide polymer, a fatty alcohol, and mixtures thereof. In one aspect, the thickener can comprise a polyacrylamide polymer and a fatty alcohol.

As used herein, "polyacrylamide polymer" refers to a polymer derived from at least one acrylamide, methacrylamide, alkyl acrylamide, or alkyl methacrylamide monomer. The polyacrylamide polymer can be a homopolymer or copolymer and linear, branched, or cross-linked. Suitable monomers for synthesizing polyacrylamide polymers can include acrylamide, methacrylamide, alkyl acrylamides, alkyl methacrylamides, anionic acrylamides, N-vinylpyrrolidone, and mixtures thereof. It can be preferred that the polyacrylamide polymer be synthesized from at least about 50 wt %, or at least about 70 wt %, or at least about 90 wt % acrylamide, methacrylamide, and mixtures thereof.

Alkyl acrylamide and alkyl methacrylamide are monomers in which the amide nitrogen is substituted with one $C_1$ to $C_{20}$ alkyl group or two $C_1$ to $C_8$ alkyl groups (preferably methyl, ethyl, or propyl), including N-methacrylamide, N-methylmethacrylamide, N-isopropylacrylamide, N-isopropylmethacrylamide, N-octyl acrylamide, N-tert-butyl acrylamide, N-phenyl acrylamide, N-sec-butyl acrylamide, N,N-dimethylmethacrylamide, and N,N-dimethylacrylamide. The polyacrylamide polymer may be synthesized using from about 0 to about 25 wt % of an alkyl acrylamide or alkyl methacrylamide monomer, alternatively from about 0.1 to about 15 wt %, alternatively from about 0.5 to about 10 wt %.

Anionic acrylic monomers can include acrylamidoalkylsulfonic acids and salts thereof. A preferred example is 2-Acrylamido-2-methylpropane sulfonic acid and salts thereof. The polyacrylamide polymer may be synthesized using from about 0 to about 10 wt % of an acrylamidoalkylsulfonic acid monomer or salt thereof, alternatively from about 0.1 to about 5 wt %, alternatively from about 0.25 to about 2 wt %.

The polyacrylamide polymer can be synthesized with less than about 10 wt % acrylates, methacrylates, maleic anhydride, and/or vinyl acetate monomers, alternatively less than about 5 wt %, alternatively substantially free of the aforementioned monomers. It is more preferred for the polymer synthesis be free of acrylic acid and methacrylic acid monomers. Without wishing to be bound by theory, polymers with strong hydrogen bonding groups like —COOH, salts of —COOH, and —OH may cause the polymer to behave as a mucoadhesive. Acrylic acid and methacrylic acid contain —COOH moieties and acrylates, methacrylates, maleic anhydride, and vinyl acetate monomers, when hydrolyzed, will also contain these hydrogen bonding moieties.

The polyacrylamide polymer may further comprise a cross-linking agent. Suitable cross-linking agents are molecules with two or more, preferably two to four, vinyl moieties. Suitable cross-linking agents can include N,N'-methylene-bisacrylamide, divinyl benzene, triallylamine, trimethallylamine, allyldimethallylamine, diallylmethallylamine, butadiene, 1,7-octadiene, allyl-acrylamides, allyl-methacrylamides, bisacrylamidoacetic acid, salts thereof, and mixtures thereof. One preferred cross-linking agent is N,N'-methylenebisacrylamide. In one aspect, the cross-linking agent can be present at a level of from about 25 to about 250,000 ppm, alternatively from about 50 to about 100,000 ppm, alternatively from about 100 to about 50,000 ppm.

The polyacrylamide polymer can have a weight average molecular weight of greater than about 1,000,000 g/mol, preferably greater than about 1,5000,000 g/mol, and can range up to about 30,000,000 g/mol.

Suitable polyacrylamide polymers can include Creagel® EZ 7 and Creagel® EZ PFC (available from The Innovation Company, Dreux Cedex, France), CustoPoly® E-5 and CustoPoly® 305 (available from Custom Ingredients, Inc., San Clemente, Calif.), Endicare® ETP305 and Endicare® ETP505 (available from Coast Southwest Inc., Placentia, Calif.), Flocare™ T 920 GC from SNF S.A.S. (France), HallGel 305 from The Hallstar Company (Chicago, Ill.), and Sepigel™ 305 and Sepigel™ 501 from Seppic Corporation (Fairfield, N.J.). Most preferred among these polyacrylamide polymers is the polymer given the CTFA designation polyacrylamide and isoparaffin and laureth-7, available under the Tradename Sepigel™ 305 from Seppic Corporation, which is synthesized using acrylamide, 2-Acrylamido-2-methylpropane sulfonic acid and cross-linked with N,N-methylenebisacrylamide.

The thickener can comprise a fatty alcohol. In one aspect, fatty alcohols can have a melting temperature of greater than 30° C., alternatively greater than about 37° C., alternatively greater than about 50° C. The melting temperature of the fatty alcohols can be measured according to the drop melting point method of ASTM D127 (Jan. 1, 2015). Non-limiting examples of fatty alcohols can include stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. In one aspect, the vaginal care composition can comprise a fatty alcohol selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred, the vaginal care composition can comprise a fatty alcohol selected from the group consisting of stearyl alcohol, cetyl alcohol, behenyl alcohol and mixtures thereof. Alternatively, the fatty alcohol can be selected from the group consisting of saturated $C_{16}$ to $C_{30}$ fatty alcohols, saturated $C_{16}$ to $C_{30}$ ethoxylated fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting temperature of at least about 45° C. In one aspect, the vaginal care composition can comprise a mixture of two or more fatty alcohols.

The vaginal care composition can comprise from about 0.1% to about 5% of a fatty alcohol alternatively from about 0.5% to about 2.5%, alternatively from about 0.75% to about 2%, all by weight of the vaginal care composition. Without being limited by theory, it is believed that these fatty alcohols can help in the formation of the rheological characteristics of the composition which can contribute to the physical stability of the composition. It is believed that the fatty alcohol can increase the viscosity of the vaginal care composition at room temperature, allowing the vaginal care composition to be applied to a delivery device and administered to the body.

While some materials such as hyaluronic acid, sodium hyaluronate, and/or other emollients may provide a desirable moisturization and/or vaginal tissue health benefit, they can also exhibit undesirable mucoadhesive characteristics when included in an aqueous vaginal care composition (e.g., stickiness). Thus, the drawbacks of including a mucoadhesive emollient may outweigh the lubricity and skin health benefit provided by such materials. However, it has now been surprisingly found that a selection of a low level of hyaluronic acid and a polyacrylamide thickener can provide an oil-in-water emulsion vaginal care composition that is stable and provides the lubrication and vaginal health benefits without the undesirable sticky feel. In some instances, it may be desirable to provide a ratio of hyaluronic acid to polyacrylamide polymer of about 1:10 to about 1:1.

The vaginal care composition may be substantially free of retinol, retinyl esters, retinaldehyde, peptides, ethanol, sunscreens, parabens, and/or sensates such as warming or cooling agents. The vaginal care composition may be substantially free of perfumes, flavorants, and/or pigments. The vaginal care composition may be substantially free of an estrogen agent and/or a progesterone agent. The vaginal care composition may be substantially free of particulates for exfoliation. In such examples, the excluded particulates have an average particle size of from about 125 microns to about 700 microns or more. Examples of such particulates may include polyethylene terephthalate (PET) microbeads, crushed apricot kernel shells, salt crystals, sugar crystals, and crushed volcanic rock. It is believed the foregoing ingredients may either be irritating or present an unsatisfactory user experience in a vaginal care composition. The vaginal care composition may be substantially free of the combination of carbomer and carbophil and other bioadhesives or mucoadhesive ingredients.

The vaginal care composition may preferably have a viscosity suitable for dispensing the composition without dripping or runniness as the user spreads the vaginal care composition about the vaginal introitus and/or external vaginal tissues. The vaginal care composition may also have a viscosity conducive to spreading onto the vaginal tissues of interest using a delivery device without undue effort. The vaginal care composition may exhibit a viscosity of from about 2,000 cps to about 200,000 cps, alternatively from about 5,000 cps to about 150,000 cps, alternatively from about 20,000 cps to about 90,000 cps, or any integer value from about 2,000 cps to about 200,000 cps, or any range formed by any of the preceding values. Alternatively, the vaginal care composition can have a viscosity of from about 20,000 cps to about 200,000 cps, alternatively from about 40,000 cps to about 100,000 cps, alternatively from about 55,000 cps to about 80,000 cps. The viscosity of the vaginal care composition can be measured according to the Viscosity Test Method described hereinafter.

It is understood that any given material may serve multiple purposes within the vaginal care composition formulation. For instance, polyethylene glycol can be used as a humectant and/or an emulsifier.

Examples

The following examples further describes and demonstrates an embodiment within the scope of the present invention. The examples are given solely for the purpose of illustration and is not to be construed as a limitation of the present invention, as many variations thereof are possible without departing from the spirit and scope of the invention. All exemplified amounts are concentrations by weight of the total composition, i.e., wt/wt percentages, unless otherwise specified.

TABLE 1

| Ingredient | Ex 1 wt. % | Ex 2 wt. % | Ex 3 wt. % | Ex 4 wt. % | Ex 5 wt. % | Ex 6 wt. % | Ex 7 wt. % |
|---|---|---|---|---|---|---|---|
| Aqueous Phase (A) | | | | | | | |
| Distilled Water | 67.1 | 64.0 | 62.6 | 64.9 | 55.1 | 59.9 | 63.14 |
| Glycerin | 8.0 | 12.0 | 5.0 | 6.0 | 10.0 | 10.0 | 10.00 |
| Sodium Hyaluronate[1] | 0.1 | 1.0 | 2.0 | 0.5 | 0.5 | 1.0 | 0.50 |
| Disodium EDTA[2] | 0.1 | 0.2 | 0.1 | 0.1 | 0.1 | 0.1 | 0.10 |
| Sodium Benzoate | 0.0 | 0.2 | 0.2 | 0.2 | 0.0 | 0.1 | 0.18 |
| Sodium salicylate | 0.2 | 0.0 | 0.2 | 0.0 | 0.3 | 0.1 | 0.0 |
| Oil Phase (B) | | | | | | | |
| Cocos Nucifera (Coconut) Oil | 0.2 | 0.2 | 0.2 | 0.5 | 0.5 | 0.5 | 0.20 |
| Helianthus Annuus (Sunflower) Seed Oil | 0.1 | 0.1 | 0.1 | 0.0 | 0.1 | 0.5 | 0.10 |
| Carthamus Tinctorious (Safflower) Seed Oil | 0.1 | 0.1 | 0.1 | 1.5 | 0.0 | 1.0 | 0.10 |
| Stearyl Dimethicone[3] | 0.0 | 0.1 | 2.0 | 5.0 | 3.0 | 0.0 | 1.00 |
| Tocopheryl Acetate (Vitamin E) | 0.2 | 0.5 | 0.5 | 0.7 | 1.0 | 0.2 | 0.50 |
| Cetearyl Glucoside, Cetearyl Alcohol[4] | 0.3 | 0.2 | 0.2 | 0.4 | 0.2 | 0.3 | 0.20 |
| Cetyl Alcohol | 0.5 | 0.7 | 0.6 | 0.7 | 0.6 | 0.5 | 0.64 |
| Stearyl Alcohol | 1.2 | 1.0 | 0.9 | 1.1 | 0.9 | 1.2 | 0.96 |
| Behenyl Alcohol | 0.8 | 0.8 | 0.8 | 0.5 | 1.2 | 0.5 | 0.80 |
| Polymethylsilsesquioxane[5] | 1.0 | 0.5 | 0.1 | 0.0 | 0.0 | 2.0 | 0.25 |
| Peg-100 Stearate[6] | 0.1 | 0.1 | 0.1 | 0.1 | 0.2 | 0.2 | 0.10 |
| Acidic Aqueous Phase (C) | | | | | | | |
| Distilled Water | 10.0 | 11.0 | 14.0 | 9.0 | 15.0 | 10.0 | 10.96 |
| Citric Acid | 0.5 | 0.5 | 0.5 | 0.5 | 0.5 | 0.5 | 0.48 |
| Sodium Citrate | 0.6 | 0.6 | 0.6 | 0.6 | 0.6 | 0.6 | 0.59 |
| D-Panthenol | 1.0 | 0.0 | 1.0 | 0.5 | 2.0 | 1.0 | 1.00 |
| Niacinamide | 0.0 | 1.0 | 3.0 | 2.5 | 5.0 | 4.0 | 3.00 |
| Other Ingredients (D) | | | | | | | |
| Polyacrylamide(and)C13-14 Isoparaffin(and)Laureth-7[7] | 2.5 | 3.0 | 3.0 | 3.5 | 1.0 | 4.5 | 3.00 |
| Phenoxyethanol | 0.2 | 0.0 | 0.0 | 0.0 | 0.0 | 0.1 | 0.0 |
| Dimethicone and Dimethiconol[8] | 5.0 | 2.0 | 2.0 | 1.0 | 2.0 | 1.0 | 2.00 |
| Sorbitan Caprylate[9] | 0.2 | 0.2 | 0.2 | 0.2 | 0.2 | 0.2 | 0.20 |

[1]Available as Bio-Sodium Hyaluronate Powder from SK Bioland (South Korea).
[2]Available as Dissolvine ® Na2-S from Akzo Nobel Functional Chemicals (Chicago, IL).
[3]Available as Silwax ® D118 from Siltech (Toronto, Ontario, Canada).
[4]Available as Emulgade ® PL68/50 from BASF (Cincinnati, OH).
[5]Available as CF600 from Momentive Performance Materials (Waterford, NY).
[6]Available as Lipopeg ® 100-S from Lipo Chemicals (Warren Township, NJ).
[7]Available as Sepigel™ 305 from Seppic (Fairfield, N.J.).
[8]Available as DC 1503 from Dow Corning ® Corp. (Carrollton, KY).
[9]Available as VELSAN ® SC from Clariant (Muttenz, Switzerland).

One and a half kilogram batches of Examples 1-7 can be made gravimetrically according to the following procedure:

Aqueous Phase (A) is prepared by combining all ingredients in a beaker or pot and heating to about 70° C. to 80° C. while stirring with an overhead mixer. Oil Phase (B) is prepared in a separate beaker or pot with a magnetic stir bar by combining all ingredients in Oil Phase (B) and heating to about 70° C. to 80° C. while stirring with a magnetic stir plate. Acidic Aqueous Phase (C) is prepared in yet another beaker or pot with a magnetic stir bar by combining all ingredients and heating to 40° C. while stirring with a magnetic stir plate.

Once Oil Phase (B) reaches about 70° C. to 80° C., it is poured into the Aqueous Phase (A) and is milled with a Tekmar mill for 5 minutes at about 5,000 rpm to 10,000 rpm, creating an oil-in-water emulsion. After milling, the heat is turned off and the mixture is allowed to cool while stirring with an overhead mixer. When the mixture reaches 60° C., Sepigel™ 305 is added with continuous stirring using an overhead mixer. When the mixture reaches 50° C. the Acidic Aqueous Phase (C) is added with continuous stirring using an overhead mixer. When the mixture reaches about 40° C. to 45° C., the remaining Other Ingredients (D) are added and the mixture is milled with a Tekmar mill for 2 minutes at about 5,000 rpm to 10,000 rpm. The resulting oil-in-water emulsion is transferred to a storage container and cooled to room temperature.

Delivery Devices for Vaginal Care Compositions

The vaginal care compositions herein may be applied by any suitable means known for applying such products, including digitally (i.e., with the hands and/or fingers) and/or with a disposable or reusable delivery device. The user may dispense the vaginal care composition onto a finger, hand, and/or delivery device and then apply the vaginal care composition to the target vaginal tissue. Additionally or alternatively, the user may dispense the vaginal care composition directly onto the target vaginal tissue and use a finger, hand, and/or delivery device to spread the vaginal care composition. Dispensing a vaginal care composition may include pouring, dipping, squeezing, and/or spraying from a container (e.g. tube, jar, bottle, spray bottle, aerosol). Non-limiting example of delivery devices for applying a vaginal care composition can include gloves, swabs, wipes, sponges, plunger-type devices, and applicators. In one aspect, it may be preferred to use a delivery device to deliver the vaginal care composition because it can help keep the vaginal care composition from touching the user's hands.

A preferred delivery device for use in applying the vaginal care composition to the vaginal introitus and/or the external vaginal tissue is the egg-shaped applicator described hereinafter. In one aspect, the applicator can be packaged together with a vaginal care composition as a kit and sold as a packaged unit. Alternatively, the elements may be provided separately.

Figure 1:
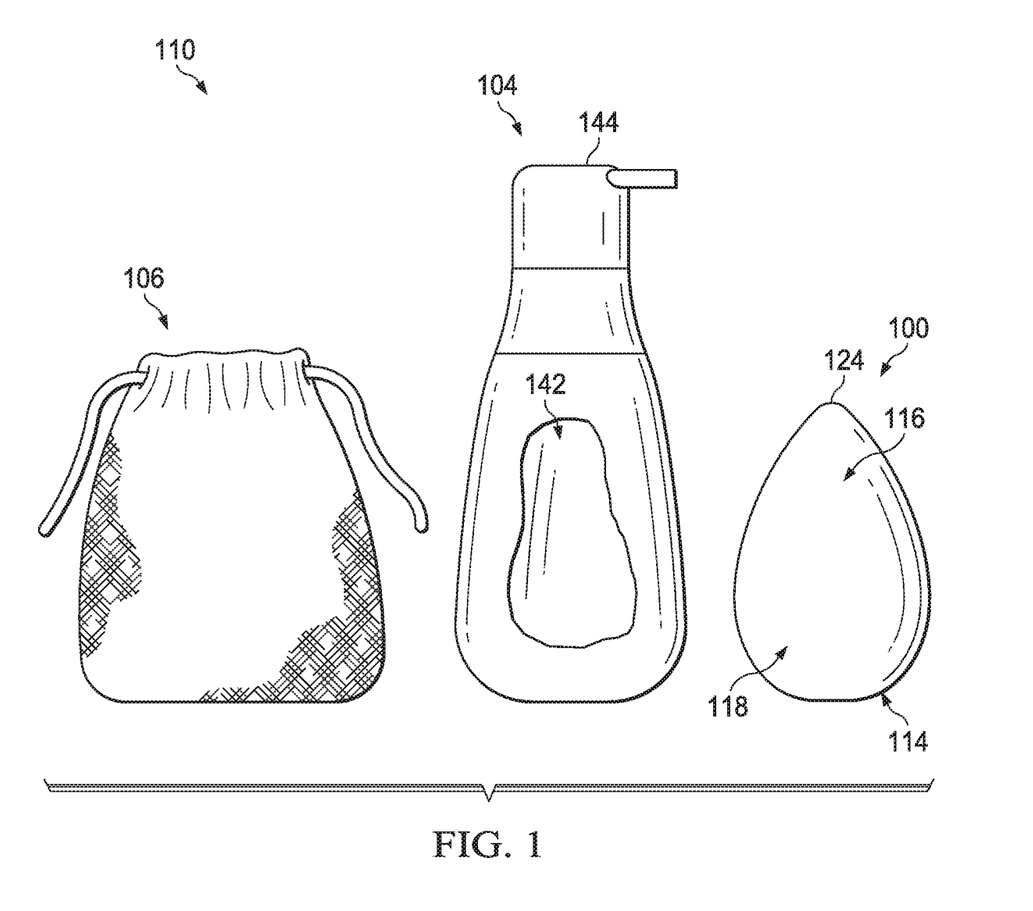
FIG. 1 is a front view of one example of a kit, including a pouch, a dispenser for a vaginal care composition, and an applicator.

As shown in FIG. 1, kit 110 can comprise applicator 100 comprising an elongate body having a proximal end 114 and an insertion portion 116 comprising tip 124 opposite proximal end 114. Applicator 100 can also comprise grippable portion 118 adjacent to proximal end 114. Kit 110 can comprise a single applicator that is reusable or a plurality of applicators may be provided. Kit 110 may further comprise dispenser 104 or receptacle (not shown). Dispenser 104 can comprise reservoir 142, in which the vaginal care composition can be stored, and a hand pump 144 for drawing the vaginal care composition from the reservoir and dispensing a dosage of the vaginal care composition from dispenser 104. Alternatively, the vaginal care composition can be stored in a chamber within applicator 100 (not shown). Kit 110 may further comprise pouch 106, in which applicator 100 and/or dispenser 104 may be stored before and after use.

Figure 2:
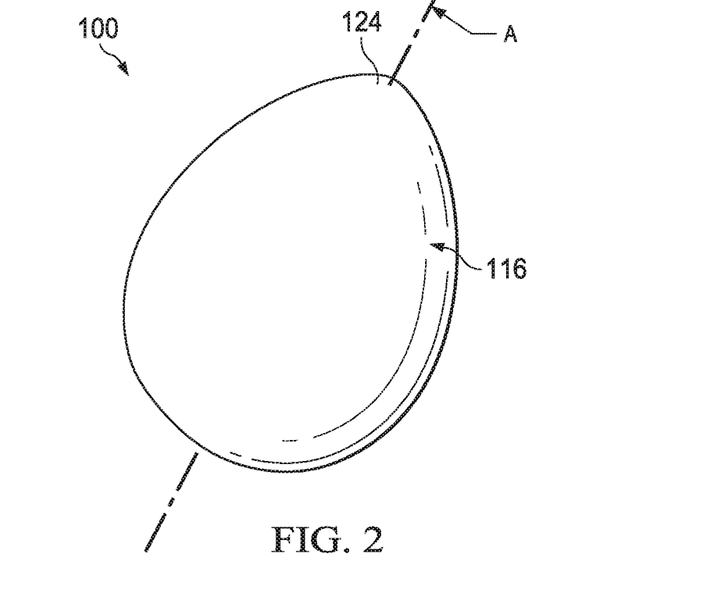
FIG. 2 is a perspective top view of the applicator of FIG. 1.
Figure 3:
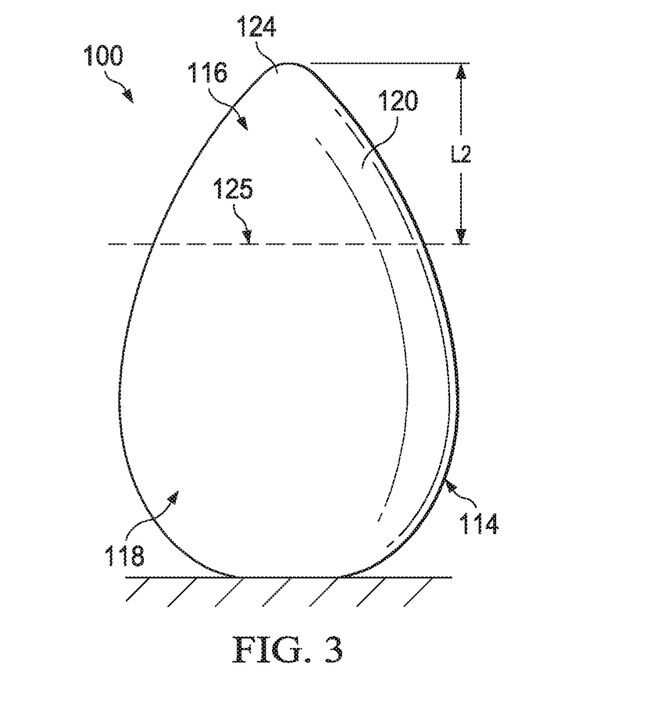
FIG. 3 is a front view of the applicator of FIG. 1 resting upright on a surface.

Referring now to FIGS. 2-3, insertion portion 116 may be shaped and sized to accommodate the anatomical geometry of the vaginal introitus and for applying the vaginal care composition thereto. Insertion portion 116 can terminate at a longitudinal distance L2 from tip 124, where the point of termination is referred to herein as base 125 of insertion portion 116. While the insertion portion may be described herein as terminating at the base for purposes of discussion, the base is not necessarily a distinct physical structure (although in some examples it may be) but rather a location along a longitudinal axis A defined by the length L2. In one aspect, insertion portion 116 may have a generally circular cross-section at base 125. Insertion portion 116 is preferably rotationally symmetrical about the longitudinal axis A, as this symmetry may facilitate easier usage and application of a vaginal care composition by a female user. In one aspect, insertion portion 116 has an overall shape that looks the same after an angular rotation thru a partial turn of 45°, 90°, 135°, 180°, 225°, 270°, or 315° about its longitudinal axis.

In one aspect, the insertion portion can be cone-shaped. Tip 124 of insertion portion 116 may have any shape, including but not limited to rounded, concave, convex, flat, indented, angled or pointed. While the insertion portion may be provided in a variety of shapes, in some examples, the insertion portion has a continual taper, has a rounded tip, a substantially circular cross section at the base and a side or lateral surface that is slightly convex from the base to the rounded tip. The lateral, outer surface (e.g., 120 in FIG. 3) of insertion portion 116 may be substantially smooth so as to avoid irritation of the vaginal tissues during manipulation of the applicator to administer the vaginal care composition to the vaginal tissues of interest.

The dimensions and structural attributes of insertion portion 116 may facilitate its use within the vaginal areas described above. While there may be considerable variability in vaginal shape, axis, and dimension from woman to woman, the dimensions and structural attributes of the insertion portion may be designed to accommodate the vaginal introitus, taking into consideration a wide range of anatomical measurements while also self-limiting the insertion depth of the applicator. Since the applicators may be used by women suffering from vaginal atrophy, the size and shape should also accommodate the anatomical changes that occur with vaginal atrophy. In one aspect, the length L2 of insertion portion 116, taken along the longitudinal axis A, may be from about 10 mm to about 25 mm, alternatively from about 10 mm to about 20 mm. In one aspect, the width of base 125 may also be the maximum width of insertion portion 116 in order to limit the distance applicator 100 is inserted into the vaginal introitus using gentle hand pressure (and without experiencing discomfort) and/or to signal to a user that the appropriate insertion depth has been achieved during use. In one aspect, it may be desirable for the applicator to be dimensioned to prevent over-insertion of the applicator into the vaginal canal. For example, insertion portion 116 or another portion of the body may further exhibit dimensions that provide a self-limiting feature with respect to insertion beyond the lower region of the vagina, such that in some examples, contact between insertion portion 116 and either of a middle region or an upper region of the vagina, including the cervix, is avoided.

Applicator 100 may also comprise grippable portion 118 adjacent proximal end 114. The grippable portion may be defined by a texture or visual indicator. The texture may comprise a plurality of protrusions, a plurality of recesses, and combinations thereof. The texture may be provided as a plurality of ridges, a plurality of grooves, and combinations of the foregoing. The grippable portion may alternatively or in addition thereto be provided with a surface finish (e.g., micro-texture) or surface treatment (e.g., dip coating, spray coating, printing) that enhances the grippability of the grippable portion. The texture, surface finish, or surface treatment may partially or wholly encircle the body. The texture may be provided as a repeating, preferably regularly repeating, pattern, although random or irregular patterns may also be provided. Further, the texture may be provided in the shape of objects, some non-limiting examples being leaves, flowers, stars, and geometric shapes. The texture may also be provided as a repeating, closed geometric shape, some non-limiting examples being circles, diamonds, triangles, rectangles, and combinations thereof. The texture, surface finish, or surface treatment may extend about 10 mm or more from the proximal end of the applicator.

Proximal end 114, or a portion thereof, may be substantially flat. As shown for example in FIG. 3, proximal end 114 of applicator 100 includes a flat portion or bottom which can allow a user to stand the applicator 100 in an upright position on a surface before and after use, such that it can be oriented in a way to minimize or prevent contact between a resting surface and the insertion portion of the applicator 100.

The overall length of applicator 100 may minimize or prevent contact between a female user's fingers and the vaginal areas described above while providing for an appropriate insertion depth slightly beyond the vaginal introitus. The length of the applicator may be from about 35 mm to about 85 mm, alternatively from about 40 mm to about 70 mm, alternatively from about 45 mm to about 65 mm, alternatively any integer value from about 35 mm to about 85 mm or any range formed by any of the preceding values.

While the applicator can be provided in a variety of overall shapes, it can be preferred that the applicator is substantially ovoidal, or egg-shaped in profile and rotationally symmetrical thru 360° of angular rotation about the longitudinal axis A thereof. It is believed this geometric shape can be desirable for application of a spreadable vaginal care composition to the vaginal introitus and optionally the vulva, vestibule, labia majora, labia minora, and/or external urogenital tract. This shape may also be particularly useful in the case of women suffering from vaginal atrophy, given the variability in shape and size of this vaginal tissue between users as well as the sensitivity of these tissues. It is also believed that this shape can facilitate grasping and manipulating the applicator by a user to apply the vaginal care composition easily while in a variety of positions (e.g., seated, standing or laying down) and without viewing the tissues of interest during use.

The applicators may be devoid of moving parts, electrically powered elements (e.g., motors, lights, circuits, buzzers, speakers, etc.) and/or electrical power sources (e.g., batteries) to provide an applicator that is simple to manufacture and also easily immersed in or rinsed with water for cleaning. An applicator that is devoid of batteries and/or electrically powered elements (e.g., motors, lights, etc.) is referred to as a non-electrical applicator. At least 60%, 70%, 80%, 90%, 95% or 100% of the bulk volume can be solid volume. The body may be devoid of chambers for storing a flowable composition and/or passages, conduits, channels and/or openings or ports for delivering such a composition to an outer surface thereof. Alternatively, the applicator can comprise a chamber for storing a flowable composition and/or passages, conduits, channels and/or openings or ports for delivering such a composition to the outer surface thereof (e.g., the insertion portion or its tip). In one aspect, the applicator can comprise a chamber in fluid communication with an opening defined on the insertion portion or tip. In one aspect, the body may be devoid of plungers and other structures that may be used to expel a vaginal care composition from the body of the applicator. Alternatively, the applicator can comprise a plunger or other structure that can be used to expel a vaginal care composition from the body of the applicator. In one aspect, the body of the applicator is not phallic shaped.

The applicator and/or the materials used to form the applicator, may exhibit one or more properties suitable for applying a vaginal care composition to the vaginal introitus and, optionally, the external vaginal tissue, some of which may be more delicate, sensitive, or fragile in women with vaginal atrophy. The applicator and/or the materials used to form the applicator may also be facilitate the grippability, re-usability, and cleanliness of the applicator. Examples of suitable materials can include one or more of a thermoplastic elastomer, a natural rubber, a synthetic rubber (e.g., a silicone elastomer/silicone rubber), a polyester (e.g., a polyurethane, such as STERALLOY® 2021-5 available from Hapco, Inc.) and/or a thermoplastic olefin.

The applicator may further comprise one or more visual indicators to indicate to the user, for example, where to hold the applicator, which end of the applicator is "up" or "down", and/or which surfaces of the applicator to which the vaginal care composition should be applied. The visual indicator can comprise colors, micro-textures, patterns, text, graphics, coatings, and combinations thereof. In one aspect, the visual indicator can be a dosing indicator that visually indicates to a user the surface of the body onto which the vaginal care composition is applied or an insertion indicator that visually indicates to user how far the body should be inserted into the vaginal introitus. The dosing indicator and/or the insertion indicator may form part of the insertion portion. Preferably, the dosing indicator is visually distinct from the insertion indicator. For example, the dosing indicator may be provided in the form of a first color while the insertion indicator might be provided as a second color different from the first color. Alternatively, the dosing indicator and the insertion indicator can be the same visual indicator. The visual indicators may be printed on the body, in molded with the body or be in the form of a coating applied to the body.

The vaginal care composition may be stored within a dispenser or a receptacle (not shown). The receptacle may be any of a jar, a bowl, a cup, or any of a variety of suitable receptacles, which may employ a screw-on lid or closure. In such examples, the insertion portion can be dipped into the receptacle to contact the vaginal care composition to transfer the vaginal care composition to a surface of the applicator.

The applicator and the dispenser storing the vaginal care composition may be packaged together as a unit for sale to a consumer. Some suitable packages may include boxes, cartons, and clamshell packages formed from plastic and/or a paper material. The kit may further include a container, such as, for example, a drawstring pouch or bag (e.g., 106), for storing one or more of the applicator and, optionally, the dispenser in between uses by a consumer. However, it will be appreciated that a container may be any of a variety of suitable containers or cases for storing one or more items associated with a kit. In some examples, the container may facilitate hygiene by maintaining cleanliness of the applicator between uses.

A particularly suitable applicator is further described in U.S. Provisional Patent Application No. 62/622,298 filed on Jan. 26, 2018, which is herein incorporated by reference in its entirety.

Methods of Use

The kits, delivery devices, and vaginal care compositions may be used in a variety of ways. In one aspect, the vaginal care composition can be administered to reduce the feeling of vaginal dryness. Alternatively, the vaginal care composition can be administered to restore vaginal moisture and lubrication.

Also described herein are methods of providing one or more vaginal health benefit comprising administering the vaginal care composition to the vaginal introitus and, optionally, external vaginal tissues such the vulva, vestibule, labia majora, labia minora, or external urogenital tract. The one or more vaginal health benefit can be selected from the group consisting of providing natural moisture; reducing vaginal irritation and/or burning; providing natural lubrication; soothing vaginal dryness; replenishing vaginal moisture; supplementing the body's natural lubrication; providing all day vaginal moisture and/or lubrication; reducing pain during sex; relieving the discomfort associated with vaginal dryness; and combinations thereof.

Also described herein are method of treating vaginal dryness and/or vaginal atrophy.

While a method of reducing the feeling of vaginal dryness is exemplified, it should be understood that the methods described herein can also be used to restore vaginal moisture and lubrication, to provide one or more vaginal health benefit, to treat vaginal dryness, and/or to treat vaginal atrophy.

In one aspect, the method for reducing the feeling of vaginal dryness can include a female user grasping the delivery device, depositing an amount of a vaginal care composition on at least a portion the delivery device, manipulating the delivery device to administer the vaginal care composition to her vaginal introitus and, optionally, one or more of the vulva, vestibule, labia majora, labia minora, or external urogenital tract, with the delivery device such that at least a portion of the vaginal care composition thereon is transferred to the vaginal tissues of interest.

In one aspect, the method for reducing the feeling of vaginal dryness can include a female user grasping the delivery device and manipulating the delivery device to administer the vaginal care composition to her vaginal area.

In one aspect, the method for reducing the feeling of vaginal dryness can include a female user holding or grasping an applicator and applying an amount of the vaginal care composition to at least a portion of the insertion portion, preferably the dosing surface, of the applicator, manipulating the applicator to administer the vaginal care composition to her vaginal introitus and, optionally, external vaginal tissues, with the applicator such that at least a portion of the vaginal care composition thereon is transferred to the vaginal tissues of interest.

In some examples where the applicator comprises a dosing indicator and/or an insertion indicator, the female user may use those indicators as a guide as to where to deposit the vaginal care composition on the applicator (e.g., the dosing surface) or how far to insert the body into her vaginal introitus during use. In some examples, the dosing indicator may provide both visual cues to the female user (i.e., the same visual indicator functions as both a dosing indicator and an insertion indicator for the female user).

The method may further include dispensing the vaginal care composition from the dispenser 104. In such examples, the vaginal care composition may be dispensed onto the insertion portion. The dispenser 104 may regulate an amount of the vaginal care composition released therefrom. The amount of the vaginal care composition released by the dispenser 104 may be the single dose sufficient for covering the insertion portion or a lesser amount such that multiple actuations (e.g., 2-4) of the dispenser are needed to provide a suitable amount.

Alternatively, the method can include the female user dispensing the vaginal care composition from a chamber within the applicator, for example by squeezing or using a plunger or pump, such that the vaginal care composition is provided on at least a portion of the external surface of the applicator.

Alternatively, the vaginal care composition can be stored within a receptacle (not shown), such as a jar or can. The insertion portion can be dipped into the receptacle to contact the vaginal care composition for application thereon. While the method has been described in association with use of the applicator, it will be appreciated that in some examples, a method for reducing the feeling of vaginal dryness may include applying a vaginal care composition to at least one digit (e.g., finger or thumb) of a female user and administering the vaginal care composition to the vaginal introitus and, optionally, the external vaginal tissue using her at least one digit.

The amount of vaginal care composition applied to the insertion portion surface may be enough to cover the insertion portion surface but not so much that dripping of the vaginal composition from the insertion portion is induced. The amount of the vaginal care composition applied to the insertion portion can be from about 0.1 g to about 2 g, alternatively from about 0.2 g to about 1.5 g, alternatively from about 0.5 g to about 1 g.

The female user may manipulate the applicator in variety manners. The female user may insert the insertion portion into her vaginal introitus using gentle handle pressure (e.g., until slight resistance to insertion is noticed by the user) so as to not over insert the body thru the vaginal introitus. The body of the applicator is preferably only inserted far enough to treat the vaginal introitus without discomfort. The insertion portion is inserted only so far as is comfortable to avoid pain or tearing or bleeding from the delicate tissues. The female user may insert the body into the vaginal introitus a distance of 40 mm, 35 mm, 30 mm, 25 mm or less, or from about 30 mm to about 5 mm, or from about 25 mm to about 10 mm. Preferably, the tip of the insertion portion is not inserted as far as the middle or upper region of the vaginal canal by the female user. In some examples, the tip of the insertion portion is inserted no further than the lower region of the vaginal canal. It is believed that at least some female users may find this method less intimidating and/or more simple and convenient, thereby encouraging long term habit adoption and compliance. The body of the applicator may then be retracted to administer any remaining vaginal care composition thereon (and/or to spread some of the vaginal care composition applied to the vaginal introitus) to the external vaginal tissues, such as labia minora, labia majora, the clitoris, the perineum, the urogenital tract, etc. In one aspect, the female user may manipulate the applicator by inserting the body into the vaginal introitus and rotating the body of the applicator using her wrist, retracting the body from the vaginal introitus and then swiping the body along the external vaginal tissues.

In some examples, the female user may administer the vaginal care composition to the vaginal tissues of interest for a period of time from about 1 second to about 40 seconds, or about 1 second to about 30 seconds, or from about 1 second to about 15 seconds, or any range formed by any of the preceding values. A short administration time is desirable for providing a method that is convenient and quick to complete.

Since the experience of both the applicator and vaginal care composition may be useful for encouraging long term habit adoption by a female user for both acute and chronic treatment of vaginal dryness and/or vaginal atrophy, the female user may use the applicator to apply the vaginal care composition on a regular basis versus as a mere precursor to sexual intercourse. For example, the method of use may not be immediately followed by sexual intercourse. Further, sexual intercourse may not even occur within 6, 12 or 24 hours of the administration of the vaginal care composition since application of the vaginal care composition is not necessarily linked to the timing of sexual intimacy. With respect to frequency of administration, in some examples, the method may be performed by a female user at least twice per week or three, four, five, six times per week or more for a period of at least 4 weeks or 8 weeks or 12 weeks or more. In other instances, the method may be performed daily for a period of at least 4 weeks or 8 weeks or 12 weeks or more. In some instances, the female user may perform the method for 6, 8, 10, 12 months or more. The method may be performed by a female user at about the same time each day or following a daily ritual activity in order to facilitate habit adoption and habit compliance. For example, the female user may perform the method in the morning, as part of a routine (e.g., after showering). Similarly, a female user may perform the method in the evening before bed or at any other time convenient to the female user. Alternatively, the method may be performed multiple times per day or as needed.

The methods may further include cleaning the applicator so that the applicator may be reused at a later time to repeat administration of the vaginal care composition. In some examples, the applicator may be rinsed, sprayed or immersed in a liquid and/or wiped with a substrate to remove any residual vaginal care composition or bodily fluids. The cleaning liquid may comprise water and, optionally, one or more adjuncts such as, for example, a soap or other surfactant. The applicator may be immersed in a container containing the cleaning liquid or merely rinsed or immersed in tap water, for example. Following the rinsing, spraying or immersion step, the applicator may be dried with a substrate or appliance (e.g., hair dryer) or left to air dry, and the applicator stored in a protective in a reusable container/package (e.g., the drawstring pouch shown in FIG. 1) for cleanliness until the next use. The cleaning step may be performed prior to application of the vaginal care composition to the applicator, subsequent to administration of the vaginal care composition to desired vaginal tissue, or both. Alternatively, the applicator may be disposable or intended for a single use.

The methods described herein may be directed to and/or performed by women experiencing vaginal dryness and/or vaginal atrophy and/or suffering from a reduction in estrogen levels. Vaginal dryness or irritation may also be due to, for example, vaginitis, inflammation of the vaginal tissue due to thinning and shrinking of the tissues, sexual arousal disorder, menopause, drug (prescription or over the counter) induced vaginal dryness, dyspareunia, sexual pain disorder, pregnancy, breast feeding, hormone imbalance, anxiety, and diabetes. In addition, the kits and vaginal care compositions may have non-medical uses for females in need of vaginal lubrication. Vaginal atrophy (sometimes referred to as atrophic vaginitis or vaginitis, vulvovaginal atrophy, or urogenital atrophy) may be characterized by thinning and shrinking of tissues as well as decreased lubrication, typically induced by a reduction in estrogen which happens naturally in perimenopausal, menopausal and post-menopausal women. Symptoms may include vaginal soreness, itching, dryness, and painful intercourse. In some examples, the female user is 30, 40, 45, 50, or 55 years of age or older, experiencing a reduction in estrogen levels, suffering from vaginal atrophy, vaginal dryness, has undergone a hysterectomy, and/or is perimenopausal, menopausal or post-menopausal. It is believed that performance of the methods described herein using an applicator and vaginal care composition may provide the female user with an acute and/or a chronic reduction in one or more of vaginal dryness, pain during sexual intercourse, vaginal itching, and vaginal irritation.

Exemplary methods of using an implement to apply a vaginal care composition are also disclosed in U.S. Provisional Ser. No. 62/622,298, which is herein incorporated by reference in its entirety.

Viscosity Test Method

The viscosity of samples is measured using Brookfield RV viscometer fitted with a helipath T-bar spindle type T-C. The viscometer is leveled, set up, and calibrated according to the manufacturer's standards. The viscometer speed (RPM) is selected to ensure the measured viscosity is within the manufactures recommended settings.

Samples are stored in sealed glass jars with an opening and internal diameter of at least 40 mm and filled to a height of at least 50 mm with care taken to avoid entrapped air bubbles. Centrifugation may be used to help remove entrained air. Sample jars are equilibrated at 23° C.±2° C. and about 50%±2° C. relative humidity for at least 24 hours prior to measurement.

Viscosity is measured at 23° C.±2° C. and about 50%±2% relative humidity by placing the uncapped sample jar under the viscometer and lowering the viscometer until the tip of the t-bar touches the surface of the sample. The descending helipath is turned on and a timer started once the cross-bar of the t-bar touches the surface of the sample. For 1 minute, a reading is taken every 10 seconds. The viscosity is the arithmetic average of the viscosities recorded. Care is taken to ensure the t-bar does not touch the glass jar.

Further Non-Limiting Description of the Disclosure

The following numbered paragraphs constitute a further non-limiting description of the disclosure in a form suitable for appending to the claim section if later desired.

A. A composition comprising an oil-in-water emulsion, a silicone wax having a melting temperature of from 24° C. to 50° C. and/or silicone particles having an average particle size of from 1 μm to 15 μm, and optionally a thickener comprising a polyacrylamide polymer and a fatty alcohol for use in the treatment of vaginal dryness.

B. The composition according to paragraph A for use in the treatment of vaginal dryness, wherein the silicone wax comprises stearyl dimethicone.

C. The composition according to any of the preceding paragraphs for use in the treatment of vaginal dryness, wherein the composition further comprises a silicone oil, wherein the silicone oil is selected from the group consisting of dimethicone, dimethiconol, and combinations thereof.

D. The composition according to any of the preceding paragraphs for use in the treatment of vaginal dryness, wherein the composition further comprises from 0.1% to 2% hyaluronic acid or salt thereof, by weight of the composition; and/or the composition further comprises an organic acid preservative and a salt of the organic acid preservative.

E. The composition according to any of the preceding paragraphs for use in the treatment of vaginal dryness, wherein the composition has a viscosity of from about 20,000 cps to about 200,000 cps.

F. Use of a composition comprising an oil-in-water emulsion, a silicone wax having a melting temperature of from 24° C. to 50° C. and/or silicone particles having an average particle size of from 1 µm to 15 µm, and optionally a thickener comprising a polyacrylamide polymer and a fatty alcohol as a vaginal care composition for restoring vaginal moisture and/or lubrication.

G. The use according to paragraph F, wherein the silicone wax comprises stearyl dimethicone.

H. The use according to paragraphs F or G, wherein the composition further comprises a silicone oil, wherein the silicone oil is selected from the group consisting of dimethicone, dimethiconol, and combinations thereof.

I. The use according to paragraphs F to H, wherein the composition further comprises from 0.1% to 2% hyaluronic acid or salt thereof, by weight of the composition and/or the composition further comprises an organic acid preservative and a salt of the organic acid preservative.

J. The use according to paragraphs F to I, wherein the composition has a viscosity of from about 20,000 cps to about 200,000 cps.

K. The use according to paragraphs F to J, wherein the composition comprises an organic acid preservative and a salt of the organic acid preservative.

L. A method of reducing the feeling of vaginal dryness, the method comprising the step of administering a vaginal care composition to the vaginal area of a female user in need thereof; wherein the vaginal care composition comprises oil-in-water emulsion, a silicone wax having a melting temperature of from 24° C. to 50° C. and/or silicone particles having an average particle size of from 1 µm to 15 µm, and optionally a thickener comprising a polyacrylamide polymer and a fatty alcohol.

M. The method according paragraph M, comprising the following steps: providing an amount of the vaginal care composition to at least a portion of an outer surface of an applicator, and administering at least a portion of the amount of the vaginal care composition to the vaginal introitus and, optionally, one or more of the vulva, vestibule, labia majora, labia minora, and/or external urogenital tract while grasping and manipulating the applicator, preferably inserting a portion of the applicator into the vaginal introitus a distance of about 35 mm or less.

N. The method according to paragraph M, wherein the amount of vaginal care composition applied to the applicator is from 0.1 g to 2 g.

O. A kit for reducing the feeling of vaginal dryness comprising:
   a. an applicator for reducing the feeling of vaginal dryness comprising a non-electrical, elongate body comprising a tapered insertion portion having a tip, a proximal end opposite the insertion portion, a dosing indicator delineating a dosing surface, and a grippable portion adjacent the proximal end; and
   a. a vaginal care composition comprising an oil-in-water emulsion, a silicone wax having a melting temperature of from 24° C. to 50° C. and/or silicone particles having an average particle size of from 1 µm to 15 µm, and optionally a thickener comprising a polyacrylamide polymer and a fatty alcohol.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing the feeling of vaginal dryness comprising:
   a. a female user providing an amount of a vaginal care composition on at least a portion of the outer surface of an egg-shaped applicator having an elongate body comprising an insertion portion and a grippable portion, wherein the egg-shaped applicator is devoid of a plunger; and
   b. administering at least a portion of the amount of the vaginal care composition to her vaginal introitus and, optionally, one or more of her vulva, vestibule, labia majora, labia minora, or external urogenital tract while grasping and manipulating the applicator;
   wherein the vaginal care composition comprises an oil-in-water emulsion and a silicone wax having a melting temperature of from about 24° C. to about 50° C.

2. The method of claim 1, wherein the silicone wax comprises stearyl dimethicone.

3. The method of claim 1, wherein the vaginal care composition further comprises silicone particles having an average particle size of from about 1 µm to about 15 µm.

4. The method of claim 3, wherein the vaginal care composition comprises polymethylsilsesquioxane particles.

5. The method of claim 3, wherein the vaginal care composition further comprises a silicone oil, wherein the silicone oil is selected from the group consisting of dimethicone, dimethiconol, and combinations thereof.

6. The method of claim 1, wherein the vaginal care composition further comprises a thickener comprising a polyacrylamide polymer.

7. The method of claim 1, wherein the vaginal care composition further comprises from about 0.1% to about 2% hyaluronic acid or salt thereof, by weight of the vaginal care composition.

8. The method of claim 1, wherein the vaginal care composition has a viscosity of from about 20,000 cps to about 200,000 cps.

9. The method of claim 1, wherein the vaginal care composition comprises an organic acid preservative and a salt of the organic acid preservative.

10. The method of claim 1, wherein the vaginal dryness is from one or more of the group consisting of vaginitis, inflammation of the vagina due to thinning and shrinking of the tissues, sexual arousal disorder, menopause, drug induced vaginal dryness, dyspareunia, sexual pain disorder, pregnancy, hormone imbalance, anxiety, or diabetes.

11. The method of claim 1, wherein the amount of the vaginal care composition applied to the applicator is from about 0.1 g to about 2 g.

12. The method of claim 1, wherein the vaginal care composition is administered once a day.

13. A kit for reducing the feeling of vaginal dryness comprising:
   a vaginal care composition and an egg-shaped applicator, wherein the egg-shaped applicator is devoid of a plunger, having an elongate body comprising an insertion portion and a grippable portion for applying the vaginal care composition to a vaginal introitus and, optionally, external vaginal tissues;
   wherein the vaginal care composition comprises an oil-in-water emulsion and a silicone wax having a melting temperature of from about 24° C. to about 50° C.

14. The kit of claim 13, wherein the vaginal care composition further comprises a polyacrylamide polymer and a fatty alcohol.

15. The kit of claim 13, wherein the vaginal care composition is stored within the applicator.

16. The kit of claim 13, wherein the vaginal care composition has a viscosity of from about 20,000 cps to about 200,000 cps.

17. The method of claim 1, wherein at least 90% of the volume of the egg-shaped applicator is solid.

18. The method of claim 1, wherein the cross-sectional area of the egg-shaped applicator is solid.

* * * * *